US009168372B2

(12) United States Patent
Fain

(10) Patent No.: US 9,168,372 B2
(45) Date of Patent: Oct. 27, 2015

(54) TEMPORARY LEADLESS IMPLANTABLE MEDICAL DEVICE WITH INDWELLING RETRIEVAL MECHANISM

(71) Applicant: PACESETTER, INC., Sylmar, CA (US)

(72) Inventor: Eric S. Fain, Menlo Park, CA (US)

(73) Assignee: PACESETTER, INC., Sylmar, CA (US)

( * ) Notice: Subject to any disclaimer, the term of this patent is extended or adjusted under 35 U.S.C. 154(b) by 126 days.

(21) Appl. No.: 13/788,891

(22) Filed: Mar. 7, 2013

(65) Prior Publication Data

US 2014/0257324 A1    Sep. 11, 2014

(51) Int. Cl.
*A61B 19/00* (2006.01)
*A61N 1/05* (2006.01)
*A61N 1/375* (2006.01)
*A61B 17/34* (2006.01)
*A61N 1/365* (2006.01)

(52) U.S. Cl.
CPC .......... *A61N 1/056* (2013.01); *A61B 17/3468* (2013.01); *A61N 1/3756* (2013.01); *A61N 1/365* (2013.01); *A61N 2001/0578* (2013.01)

(58) Field of Classification Search
USPC ....................................................... 606/129
See application file for complete search history.

(56) References Cited

U.S. PATENT DOCUMENTS

| 5,549,615 | A | 8/1996 | Hocherl et al. |
|---|---|---|---|
| 7,082,336 | B2 | 7/2006 | Ransbury et al. |
| 7,363,082 | B2 | 4/2008 | Ransbury et al. |
| 7,529,589 | B2 | 5/2009 | Williams et al. |
| 7,617,007 | B2 | 11/2009 | Williams et al. |
| 7,630,767 | B1 | 12/2009 | Poore et al. |
| 7,937,148 | B2 | 5/2011 | Jacobson |
| 8,010,209 | B2 | 8/2011 | Jacobson |
| 8,352,025 | B2 | 1/2013 | Jacobson |
| 2002/0065543 | A1 | 5/2002 | Gomperz et al. |
| 2009/0082828 | A1 | 3/2009 | Ostroff |
| 2011/0071585 | A1 | 3/2011 | Ransbury et al. |
| 2011/0270349 | A1* | 11/2011 | Cowley et al. ................. 607/45 |
| 2012/0095539 | A1* | 4/2012 | Khairkhahan et al. ........ 607/116 |
| 2012/0165827 | A1 | 6/2012 | Khairkhahan et al. |
| 2012/0172891 | A1* | 7/2012 | Lee ............................. 606/129 |
| 2012/0197349 | A1* | 8/2012 | Griswold et al. .............. 607/60 |

\* cited by examiner

Primary Examiner — Tuan V Nguyen

(57) ABSTRACT

A method and system are provided for removing, from an implant chamber of a heart, a leadless implantable medical device (LIMD) having a distal end and a proximal end. The distal end is configured to be actively secured to tissue in the implant chamber of the heart. The proximal end is configured to be coupled to a distal end of an indwelling retrieval mechanism (IRM). The IRM extends from the heart along a vessel, the IRM having a proximal end configured to be anchored at a temporary anchor site. The method comprises detaching the IRM from the anchor site, loading a retrieval tool over the proximal end of the IRM and along the body of the IRM. The retrieval tool has a lumen therein that receives the IRM as the retrieval tool re-enters the vessel, thereby allowing the retrieval tool to engage the LIMD.

6 Claims, 11 Drawing Sheets

TEMPORARY LEADLESS IMPLANTABLE MEDICAL DEVICE WITH INDWELLING RETRIEVAL MECHANISM

BACKGROUND OF THE INVENTION

Embodiments of the present invention generally relate to leadless implantable medical devices (LIMDs) and more particularly to temporary LIMDs that are implanted for a short period of time.

Recently, it has been proposed to utilize small sized devices configured for intra-cardiac implant. These devices, termed leadless implantable medical devices (LIMDs) are typically characterized by the following features: they are devoid of leads that pass out of the heart to another component, such as a pacemaker outside of the heart; they include electrodes that are affixed directly to the "can" of the device or to extensions of the device; and the device is capable of pacing and sensing in the chamber of the heart where it is implanted.

LIMDs that have been proposed thus far offer limited functional capability. These LIMDs are able to sense in one chamber and deliver pacing pulses in that same chamber, and thus offer single chamber functionality. For example, an LIMD device that is located in the right atrium offers AAI mode functionality. An AAI mode LIMD can only sense in the right atrium, pace in the right atrium and inhibit pacing function when an intrinsic event is detected in the right atrium within a preset time limit. Similarly, an LIMD that is located in the right ventricle would be limited to offering WI mode functionality. A WI mode LIMD can only sense in the right ventricle, pace in the right ventricle and inhibit pacing function when an intrinsic event is detected in the right ventricle within a preset time limit. More recently, LIMDs have been proposed that afford dual chamber pacing/sensing capability (DDD mode) along with other features, such as rate adaptive pacing.

LIMDs are being considered initially for chronic pacing patients, such as with current indications for VVIR pacing. However, another possible use for the LIMD is for temporary use, such as in the order of a few months or even less than 30 days (e.g., for patients needing peri-operative, but not chronic, pacing). The indications for such temporary LIMDs would include patients who are currently indicated for temporary pacing using an external pacer, for example patients recovering from heart surgery. As another example, it is known that a potential complication of surgical aortic valve replacement is sudden death in the month following surgery. However, the risk of sudden death could be mediated by offering a device that can support pacing during a time period when the patient may experience heart block.

One of the challenges with leadless implantable medical devices will be explant, whether for battery depletion, lack of need, infection or otherwise. Various systems are being developed to capture the proximal end of a leadless pacemaker and retrieve it. See for example Khairkhahan 2012/0165827 (Nanostim).

It is known to anchor a temporary pacemaker or intravascular defibrillator with a tether inside a vein. For example, Ostroff 2009/0082828 shows a tether anchoring the leadless pacemaker to an intraluminal stent in the inferior vena cava. An intravascular anchor with tether is also shown in Ransbury 2011/0071585.

However, conventional approaches experience certain limitations. For example, to explant conventional LIMDs, a separate extraction tool must be introduced and independently steered or manipulated along the patient's vasculature system into the heart and to a chamber in which the LIMD is implanted. The extraction tool must be independently guided by the physician. It may be difficult to align and connect the extraction tool with the LIMD. This alignment process may become unduly time consuming. Also, the physician typically utilizes a fluoroscopy system, CT system and the like to watch the position and movement of the extraction tool relative to the LIMD. Hence, the patient is exposed to a certain amount of radiation during the LIMD extraction process. The amount of radiation will vary based upon the amount of time needed, and number of images taken, in connection with attaching the extraction tool to the LIMD, detaching the LIMD from the heart tissue and extracting the LIMD.

A need remains for an extraction system and method that is efficient, not time consuming, and reduces a physician's need for fluoroscopy or CT images of the patient.

SUMMARY

In accordance with one embodiment, a method is provided for removing, from an implant chamber of a heart, a leadless implantable medical device (LIMD). The LIMD has a distal end and a proximal end. The distal end is configured to be actively secured to tissue in the implant chamber of the heart. The proximal end is configured to be coupled to a distal end of an indwelling retrieval mechanism (IRM). The IRM extends from the heart along a vessel, the IRM having a proximal end configured to be anchored at a temporary anchor site. The method comprises exposing the proximal end of the IRM by detaching the IRM from the anchor site, loading a retrieval tool over the proximal end of the IRM and along the body of the IRM. The retrieval tool has a lumen therein that receives the IRM as the retrieval tool re-enters the vessel, thereby causing the retrieval tool to track a path of the IRM through the vessel, into the heart and to the implant chamber until engaging the LIMD. The method comprises attaching a distal end of the retrieval tool to the proximal end of the LIMD, manipulating the retrieval tool such that the distal end of the retrieval tool causes the LIMD to detach from cardiac tissue within the implant chamber; and pulling at least one of the IRM and the retrieval tool to extract the LIMD from the heart.

The method is further comprised of sliding an introducer instrument over the proximal end of the IRM, until at least a portion of the introducer instrument enters the vessel, wherein the retrieval tool represents a catheter that is advanced over the IRM. The introducer instrument represents one of a needle or catheter. Optionally, the method further comprises forming the IRM of a flexible biocompatible and biostable material. Optionally, the method further comprises forming the IRM of a monofilament or multistrand suture thread. Optionally, the method further comprises including, on the IRM, a non-thrombogenic coating the IRM having a strength to survive a duration of a time in which the LIMD is implanted. Optionally, the method further comprises sliding a distal end of the retrieval tool over the IRM until the distal end of the retrieval tool engages with the proximal end of the LIMD, and manipulating the retrieval tool with respect to the LIMD to securely join the distal end of the retrieval tool to the proximal end of the LIMD. The retrieval tool and LIMD have corresponding mating features, and the method comprises securely attaching the mating features on the retrieval tool and the LIMD to one another prior to detaching the LIMD from the cardiac tissue. Optionally, the method further comprises detaching the proximal end of the IRM from at least one of subcutaneous tissue and muscle associated with the anchor site.

In accordance with one embodiment, a leadless implantable medical device (LIMD) system is provided comprised of a housing having a distal end and a proximal end, the distal end configured to be actively secured to tissue in an implant chamber of a heart with at least one electrode to perform at least one of sensing and pacing of one or more chambers of the heart. A processor controls sensing and pacing operations. An indwelling retrieval mechanism (IRM) has a distal end coupled to the proximal end of the LIMD. The IRM having a body configured to extend from the heart, along a vessel and exit the vessel at an exit/re-entry point. The IRM has a proximal end configured to be anchored at a temporary anchor site to at least one of subcutaneous tissue and muscle while the LIMD is implanted. The body of the IRM is formed of a flexible biocompatible and biostable material and has sufficient strength to maintain a desired level of structural integrity for a duration of time that the LIMD is implanted.

Optionally, the system further comprises a retrieval tool having a body with a lumen extending therethrough and an open distal end. The distal end of the retrieval tool receiving the proximal end of IRM. The IRM slides along the lumen of the retrieval tool as the retrieval tool is advanced to the LIMD. The distal end of the retrieval tool and the proximal end of the LIMD have mating features that securely attach to one another such that when rotational or longitudinal forces are applied to the retrieval tool, substantially corresponding rotational and longitudinal forces are imposed onto the LIMD to manipulate the LIMD to cause the LIMD to detach from cardiac tissue within the implant chamber. The retrieval tool includes a threaded mating feature to engage the LIMD. Optionally, the system further comprises an introducer instrument that slides over the proximal end of the IRM until at least a portion of the introducer instrument enters the vessel. A distal end is slid over the IRM until the distal end engages the proximal end of the LIMD. The retrieval tool is manipulated with respect to the LIMD to securely join the distal end of the retrieval tool to the proximal end of the LIMD.

The system securely attaches the mating features on the retrieval tool and the LIMD to one another prior to detaching the LIMD from the cardiac tissue. The retrieval tool may comprise a catheter having first and second lumen, the first lumen to receive the IRM, and an LIMD gripper device loaded into the second lumen and advanced until projecting from an open end of the catheter. A distal end of the LIMD gripper device is coupling to the proximal end of the LIMD.

DETAILED DESCRIPTION

Figure 1:
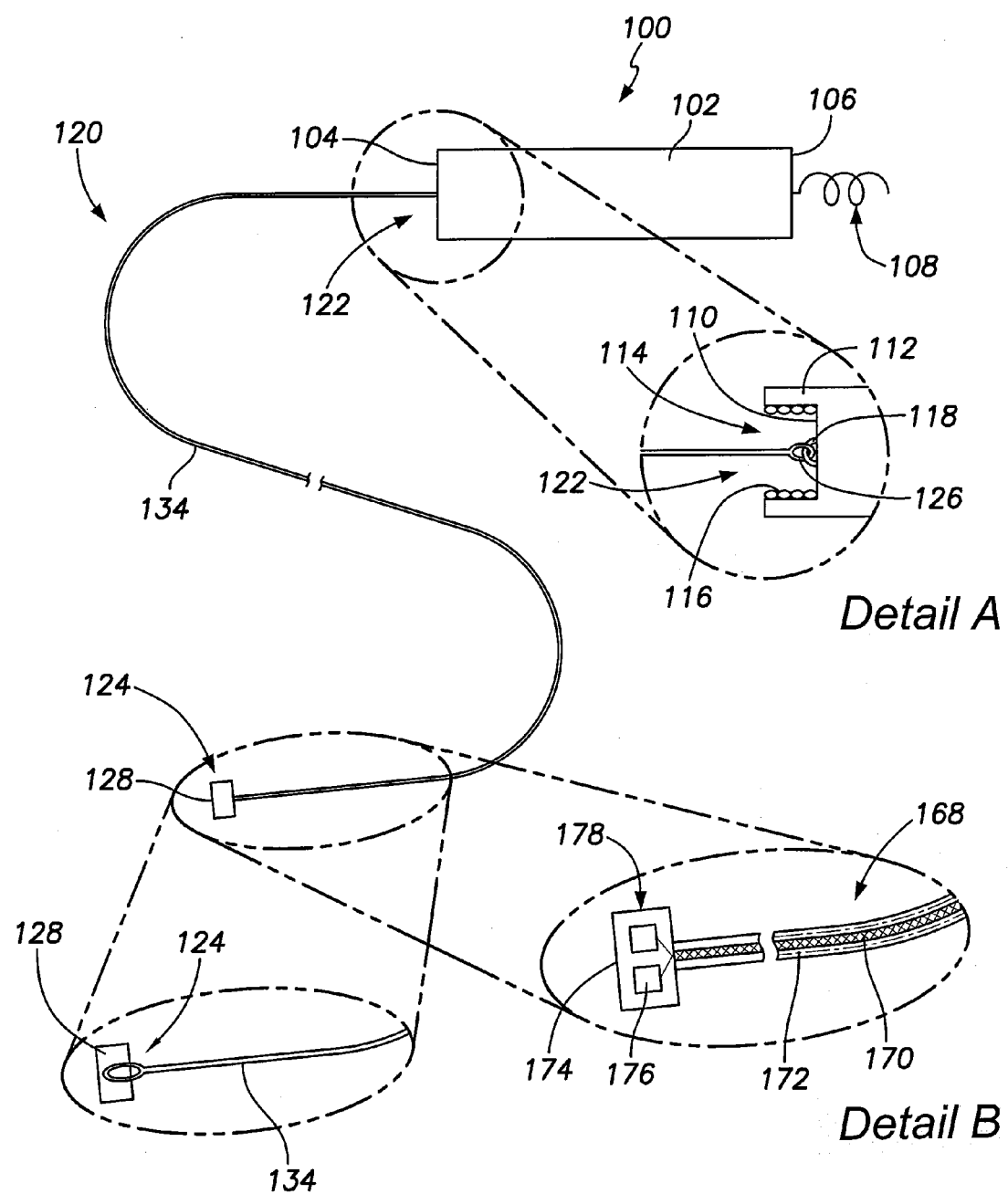
FIG. 1 illustrates an LIMD formed in accordance with an embodiment of the present invention.

Embodiments of the present invention are directed to a temporary LIMD that is joined to an indwelling retrieval mechanism to allow quick and easy explant of the LIMD. FIG. 1 illustrates an LIMD 100 formed in accordance with an embodiment of the present invention. The LIMD 100 includes a housing 102 having a proximal end 104 and a distal end 106. An active fixation member 108 is provided at the distal end 106 and is configured to be securely affixed to cardiac tissue at an implant site, such as in a chamber of the heart (also referred to as the implant chamber). Optionally, member 108 may be replaced with a passive member, such as electrode pads and the like. The LIMD 100 is configured to be temporarily implanted, such as for a few weeks, few months and the like. For example, the battery in the LIMD 100 may be relatively small, sufficient to last only a few weeks or months.

An indwelling retrieval mechanism (IRM) 120 is provided that includes a distal end 122 and a proximal end 124. The term "indwelling" is used to indicate that the retrieval member remains implanted or dwells in the patient for the entire life of the LIMD 100. The distal end 122 is permanently (e.g., for the duration of implant) connected to the proximal end 104 of the LIMD 100. The IRM 120 may represent a line or cable made of a flexible or floppy biocompatible and biostable material such as monofilament or multi-strand suture thread. The material may exhibit relatively high tensile strength with relatively low elongation under strain. For example, the material may represent ultra high molecular weight polyethylene (UHMWP). The filament or thread of the IRM 120 may have a non-thrombogenic coating, where the filament or thread of the IRM 120 is formed with strength sufficient to survive the expected implant duration.

FIG. 1 illustrates, at detail A, a more detailed view of the proximal end 104 of the LIMD 100. The proximal end 104 includes a retrieval tool engaging (RTE) interface 114 that is configured to be releasably joined to a retrieval tool (explained below) in connection with explant of the LIMD 100. By way of example, the housing 102 may include, at the proximal end 104, a peripheral rim 112 that extends beyond a top surface 110 of the housing 102. The rim 112 has a threaded surface 116 that faces inward or outward from the rim 112. The rim 112 and threaded surface 116 are positioned and dimensioned to engage mating features on the retraction tool. Optionally, the RTE interface 114 may be formed with alternative types of interfaces, other than a threaded interface, such as with a friction fit, a key-type interface and the like.

Detail A of FIG. 1 also illustrates one example of how the IRM 120 may be joined to the LIMD 100. By way of example, the distal end 122 of the IRM 120 is tied, such as utilizing a suture type knot 126, to an IRM retention element 118 formed on the top surface 110 of the housing 102. For example, the IRM retention element 118 may represent a ring, post, hook and the like. The distal end 122 of the IRM 120 is secured to the IRM retention element 118 prior to implanting the LIMD 100. Optionally, when the IRM 120 is a cable, the IRM retention element 118 may be formed in a different manner to facilitate attachment to the distal end 122 of a cable type IRM 120.

The IRM 120 has a body 134 that is sufficiently long to extend from an implant chamber of interest in the heart, along a vessel, to a remote venous implant site such as the jugular vein, subclavian vein, the femoral vein and the like.

Option A in FIG. 1 illustrates one embodiment for the IRM 120. In the example of Option A, the body 134 of the IRM 120 is formed of a suture thread that is joined to a vessel securing member 128. The proximal end 124 of the body 134 may be looped and tied, glued or otherwise attached to the vessel securing member 128. The vessel securing member 128 is shaped and dimensioned to facilitate attachment of the proximal end 124 to muscle or subcutaneous tissue outside a vessel where the body 134 of the IRM 120 can be easily accessed by the clinician at the time of retrieval. For example, the vessel securing member 128 may be formed as a patch or pad that is bonded to the proximal end 124 of the IRM 120. The patch or pad is then sutured to muscle or tissue.

The body 134 of the IRM 120 is sized to allow a guiding catheter to track over the body 134 (e.g., a filament or thread) without breaking. The body 134 should include sufficient slack within the vein so that it does not produce any stress on the LIMD 100 and/or any cardiac anatomy through which the body 134 passes.

Option B in FIG. 1 illustrates an alternative configuration for the body of the IRM 120. In option B, the IRM 120 may be formed with a compound body 168 that includes a conductive core 170 (e.g., a single strand wire or multi-strand wire). The core 170 may be made of steel or wire mesh. The core 170 may be formed with a honeycomb pattern that resists compression or along the length of the extension body. The core 170 of the IRM 120 may be configured, such as in a mesh pattern, to afford strong resistance to torque about the length of the body of the IRM 120 when turned in a rotational direction about a longitudinal length thereof. When formed in a mesh, the core 170 is flexible in a lateral direction in order to be bent side to side during implant and following implant.

The core 170 of the compound body 168 is hermetically enclosed in an insulation shell 172 provided around the core 170. For example, an insulated, flexible, biocompatible expande polytetrafluoroethylene (ePTFE) shell 172 may be formed over the core 170. Optionally, the shell 172 may be formed of PTFE, FEP, PFA (a copolymer of tetrafluoroethylene and perfluoroalkyl vinyl ether) and the like. Optionally, the insulation shell 172 may be omitted entirely such as when the core 170 is formed of a biocompatible and biostable material. In one example, the core 170 simply serves to afford good, structural integrity that is sufficient to survive for an expected time duration in which the LIMD 100 is implanted and at the time of explant to maintain its structural shape to facilitate guidance of a retrieval tool.

Optionally, when conductors are provided in the core 170, the core 170 may be configured to convey electrical communications between the LIMD 100 and an external device. For example, the core 170 may be electrically coupled at the distal end to a processor and transceiver in the LIMD 100. The core 170 may then have an external device interface 178 provided at a proximal end 174 of the IRM 120. One or more contacts 176 are provided on the external device interface 178. The contacts 176 are electrically coupled to corresponding wires in the core 170. For example, the core 170 may have one or more electrically separate wires formed individually or into a twisted pair. Proximal ends of the wires in the core 170 are joined to separate contacts 176 that engage mating contacts on an external device interface in order that the LIMB 100 can communicate over a wire based interface with an external device.

Figure 2:
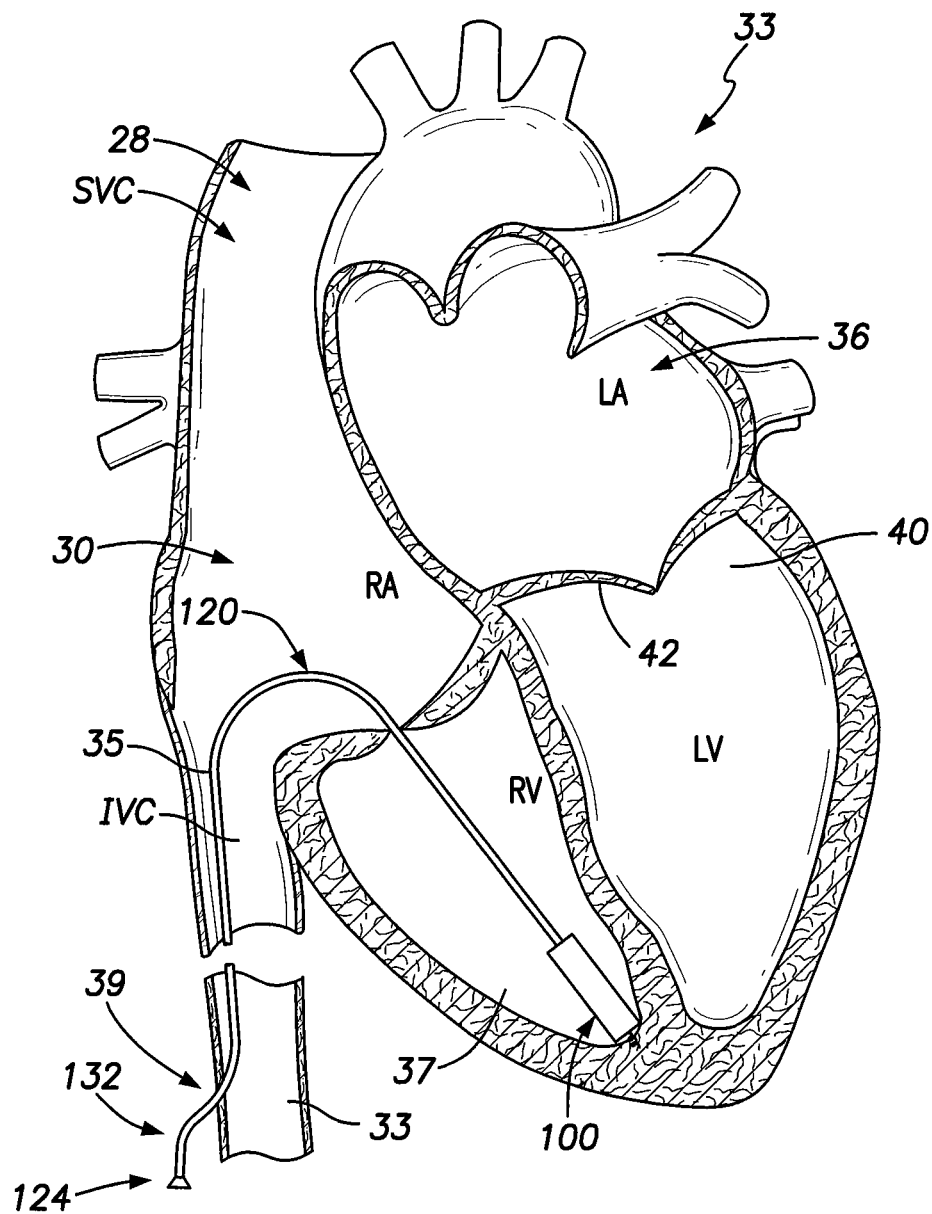
FIG. 2 illustrates the LIMD when temporarily implanted in a chamber of the heart.

FIG. 2 illustrates the LIMD 100 and IRM 120 when temporarily implanted in a chamber of the heart, such as for a few weeks, a few months or up to 1-2 years. In the example of FIG. 2, the LIMD 100 is temporarily implanted in the right ventricle (RV) 37. Optionally, the LIMD 100 may be implanted in any chamber of the heart, such as the right atrium (RA) 30, left ventricle (LV) 40 or left atrium (LA) 36. The LIMD 100, as shown, was implanted (and will be explanted) through the inferior vena cava (IVC) 35. The IRM 120 extends through the tricuspid valve 42 and into the IVC 35. The IRM 120 continues beyond the IVC 35 to a select entry/exit vessel 33 where the IRM 120 exits the vessel 33 (as denoted at 39). As one example, the vessel 33 may represent the jugular vein, subclavian vein, femoral vein and the like. The proximal end 124 of the IRM 120 is secured to subcutaneous tissue or muscle through a suture, glue type bond or other securing means.

Optionally, the LIMD 100 may be implanted (and may be explanted) through the superior vena cava (SVC) 28. In this example, the IRM 120 would extend along the SVC 28 to a select vessel where the IRM 120 exists the vessel and is similarly secured to subcutaneous tissue or muscle outside of the vessel.

Next, an explant process will be described in accordance with an embodiment for extracting the LIMD 100, at the completion of the implant period, in connection with FIGS. 3-6.

Figure 3:
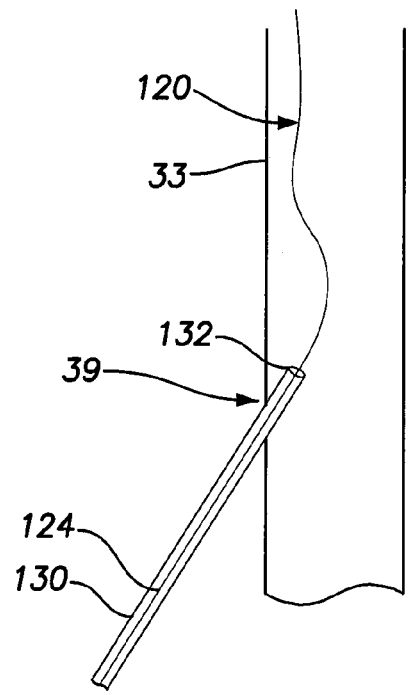
FIG. 3 illustrates a portion of the IRM and the portion of the vessel from which the IRM exits at, while at an introducer preparation stage of the explant process.

FIG. 3 illustrates a portion of the IRM 120 and the portion of the vessel 33 from which the IRM 120 exits at 39, while at an introducer preparation stage of the explant process. At a desired time of explant (e.g., when pacing support is no longer needed), the proximal end 124 of the IRM 120 is detached from the tissue or muscle. The proximal end 124 is exposed and prepared to serve as a guide to re-enter the vein. For example, the vessel securing member 128 or interface 178 (FIG. 1) may be removed. An introducer instrument 130 is slid over the proximal end 124 of the IRM 120 until at least a portion of the introducer instrument 130 enters the vessel 33. For example, the introducer element 130 may represent a hollow needle or catheter with a cutting tip. The introducer element 130 has an open tip 132 that is slid over the proximal end 124 of the IRM 120. The introducer element 130 is advanced over the IRM 120 until the introducer element 130 enters the vessel 33 through the opening 39 and extends into the vessel 33 by a desired distance. The introducer element 130 has a rigid housing that may be linear in shape. Optionally, the introducer element 130 may have a rigid housing that is formed with a predefined curve configured to facilitate entry of a retrieval tool, where the shape of the introducer element 130 is dependent on the location at which the proximal end 124 of the IRM 120 is secured to the patient's anatomy. The introducer element 130 affords a point of access to the vessel 33 without placing undue pressure on the vessel 33 or the exit/entrance opening 39 of the vessel 33.

Figure 4:
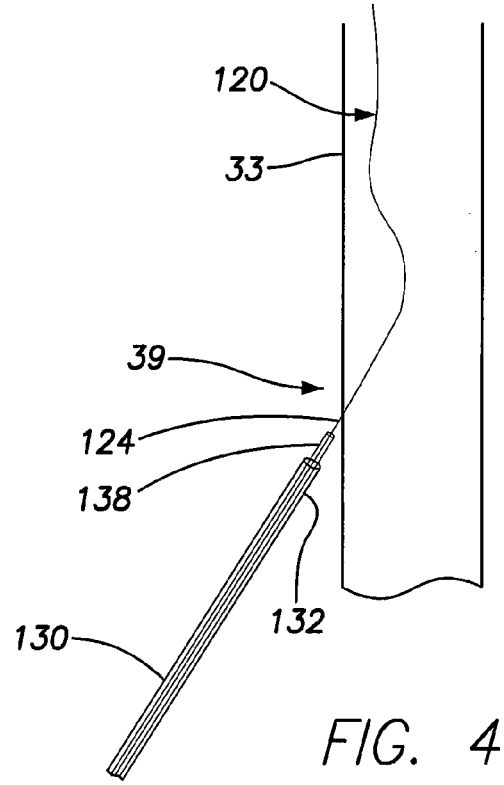
FIG. 4 illustrates an introducer preparation stage of the explant process in accordance with an alternative embodiment.

FIG. 4 illustrates an introducer preparation stage of the explant process in accordance with an alternative embodiment. In the embodiment of FIG. 4, a guidewire or similar mechanism 138 may be first attached to the proximal end 124 of the IRM 120. The introducer instrument 130 is then slid over the guidewire 138, thereby facilitating the attachment of the introducer instrument 130 to the IRM 120.

Figure 5:
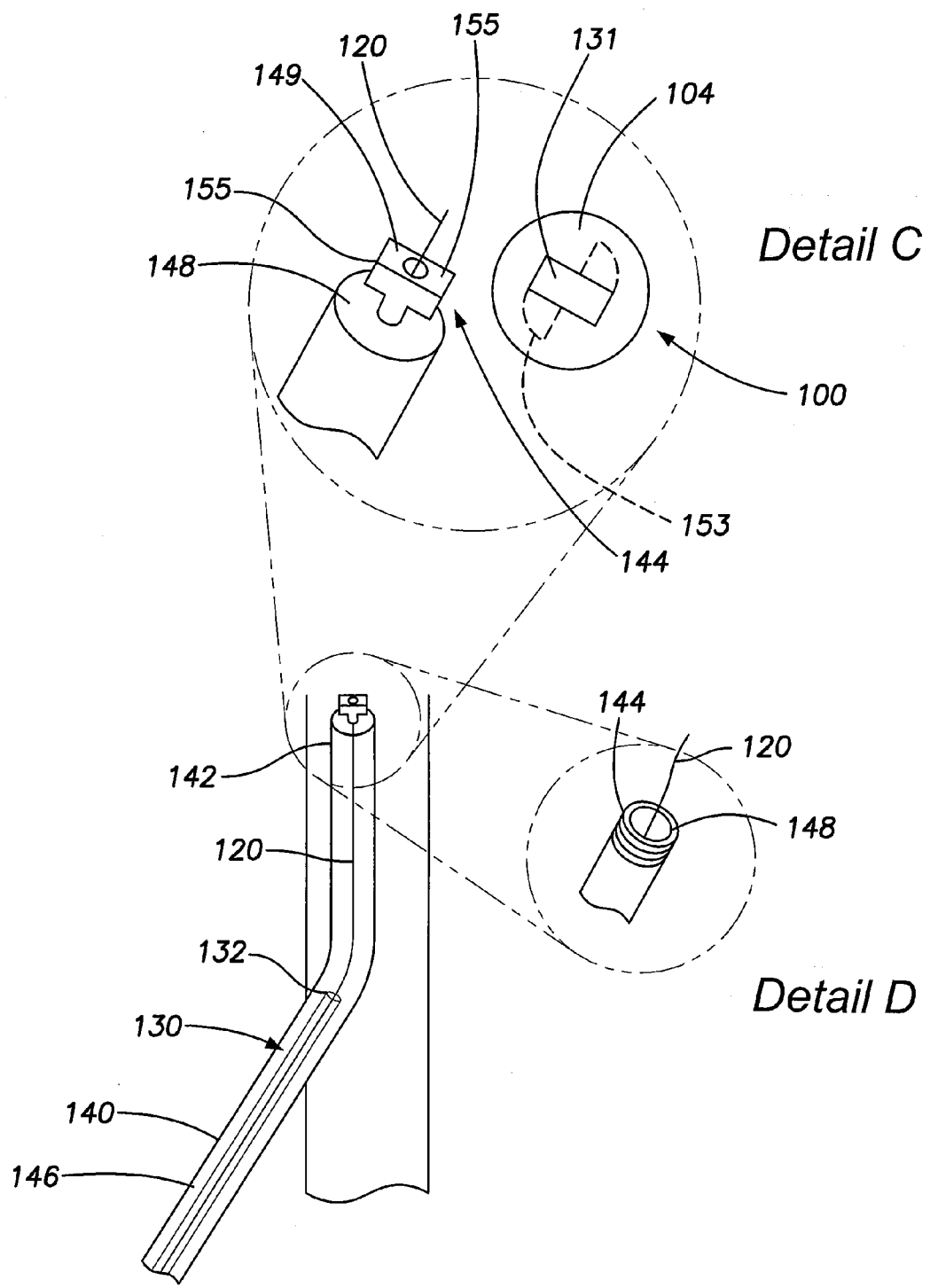
FIG. 5 illustrates an extraction tool vessel entry stage of the extraction process after gaining access to the vessel with the introducer instrument.

FIG. 5 illustrates an extraction tool vessel entry stage within the extraction process after gaining access to the vessel with the introducer instrument 130 upon completion of the introducer preparation operation. In the stage of FIG. 5, a retrieval tool 140 having a lumen 146 is loaded over the introducer instrument 130. For example, the retrieval tool 140 may represent a guiding/retrieval catheter with at least one lumen 146 extending along a length thereof. The retrieval tool 140 includes an open distal end 142 that may be loaded over a proximal end (not shown) of the introducer instrument 130. As the retrieval tool 140 enters the vessel 33 at opening 39, the retrieval tool 140 follows the substantially linear (or fixed curved) path defined by the introducer instrument 130 to align with the path of the vessel 33. The retrieval tool 140 continues to advance beyond the open tip 132 of the introducer instrument 130. The retrieval tool 140 bends to follow the path of the body 134 of the IRM 120 as the retrieval tool 140 is advanced along the vessel 33 until reaching the IVC 35 (FIG. 1) or SVC 28, entering the RA 30, passing through the tricuspid valve 42 and entering the RV 37. The lumen 146 of the retrieval tool 140 tracks over the IRM 120 until reaching the proximal end 104 of the LIMD 100 such as in an over-the-wire procedure.

Detail D in FIG. 5 illustrates the distal end 142 of the retrieval tool 140 in more detail. The retrieval tool 140 and LIMD 100 have corresponding mating features. The extraction method comprises securely attaching the mating features on the retrieval tool 140 and the LIMD 100 to one another prior to detaching the LIMD 100 from the cardiac tissue. As one example, the distal end 142 may have a threaded beveled edge 148 such as to facilitate engagement with a RTE interface 114 on the LIMD 100. As an example, the mating feature 144 may represent threads formed about the outer periphery of the distal end 142 that are configured to rotate and attach to the proximal end 104 of the LIMD 100. As shown in FIG. 1, Detail A, the proximal end 104 of the LIMD 100 includes threads 116 on a peripheral rim 112. One or both of the peripheral rim 112 and beveled edge 148 are sloped to facilitate alignment.

In the above example, the mating feature 144 and IRM retention element 118 represent mating threaded elements. Optionally, other types of interfaces may be utilized. For example, one or both of the LIMD 100 and retrieval tool 140 may have keying features. Optionally, the beveled edge 148 may be replaced with an outwardly flared coupler having threads on the interior. In this option, the rim 112 of the RTE interface 114 would be beveled inward and have threads on the exterior of rim 112 to fit into the flared threaded coupler on the distal end 142 of the retrieval tool 140.

The retrieval tool 140 is manipulated with respect to the LIMD 100 to securely join the distal end 142 of the retrieval tool 140 to the proximal end 104 of the LIMD 100. For example, the retrieval tool 140 may be manipulated by rotating the retrieval tool 140 one or more turns, such as when screw type mating features are utilized.

Detail C in FIG. 5 illustrates an alternative retrieval tool 140 with a mating feature 144 having a rectangular bar 149 extending from the distal end 142 that is shaped and dimensioned to fit into a rectangular cavity 151 in the proximal end 104 of the LIMD 100. In this alternative, the retrieval tool 140 is pushing to advance the bar 149 into the cavity 151 of the proximal end 104 of the LIMD 100 and twisted a partial turn (e.g., ¼turn, ½ turn, ¾ turn) to lock the bar 149 in the cavity 151. The cavity 151 has an interior chamber 153 (denoted in dashed lines). When the bar 149 is rotated, opposite ends 155 of the bar 149 no longer align with the opening of the cavity 151. The ends 155 may be oriented at an orthogonal (or other) angle with respect to the opening of the cavity, thereby resisting detachment of the mating feature 144 from the LIMD 100.

A physician or surgeon may operate user controls on the retrieval tool 140 at a proximal end (not shown). The proximal end may include user controls that allow the retrieval tool 140 to be bent, curved, canted, rotated, twisted, or the like, so as to be navigated through a patient's vasculature. For example, a distal end of the retrieval tool 140 may be bent, curved, canted, rotated, twisted, articulated, or the like through operation by the physician or surgeon manipulating the user controls at the proximal end of the retrieval tool 140.

Figure 6:
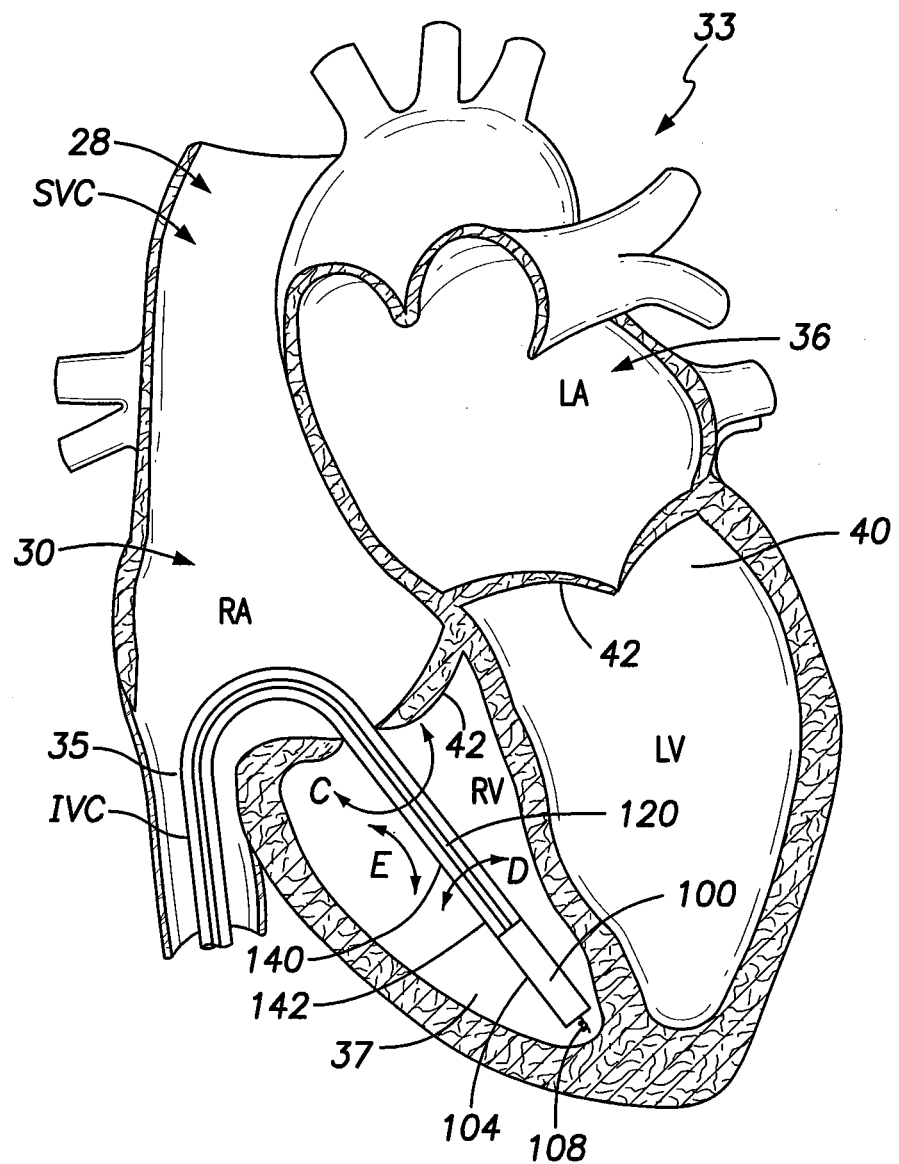
FIG. 6 illustrates a disengagement stage of the extraction process in which the retrieval tool is manipulated to detach the LIMD from the cardiac tissue within the implant chamber.

FIG. 6 illustrates a disengagement stage of the extraction process in which the retrieval tool 140 is manipulated to detach the LIMD 100 from the cardiac tissue within the implant chamber. The retrieval tool 140 is shown advanced through the SVC 35, through the tricuspid valve 42 and into the RV 37. The distal end 142 of the retrieval tool 140 abuts against and is securely engaged with the proximal end 104 of the LIMD 100. Once the retrieval tool 140 is securely attached to the LIMD 100, the retrieval tool 140 is manipulated in order to detach the active fixation member 108 from cardiac tissue. For example, when the active fixation member'108 is a helical screw, the retrieval tool 140 may be rotated about its longitudinal axis (as denoted by Arrow C) in a counterclockwise direction such as to unscrew the helix of the active fixation member 108. Optionally, the retrieval tool 140 may be rotated in the opposite direction depending upon the direction in which the helix of the active fixation member 108 is wound. Optionally, the retrieval tool 140 may be manipulated in other manners as well to detach the LIMD 100, such as by tilting the LIMD 100 to one side or the other, along or in combination with rotating the LIMD 100. Optionally, the retrieval tool 140 may simply be extracted by pulling the LIMD 100 away from the cardiac tissue.

As another example, when the active fixation member 108 is a hook or barb type element, the retrieval tool 140 may be tilted or pitched in a lateral and/or oblique direction such as denoted by Arrows D and E to tilt the LIMD 100 with respect to its longitudinal axis. By tilting the LIMD 100, this motion may partially or wholly disengage the active fixation member 108.

Figure 7A:
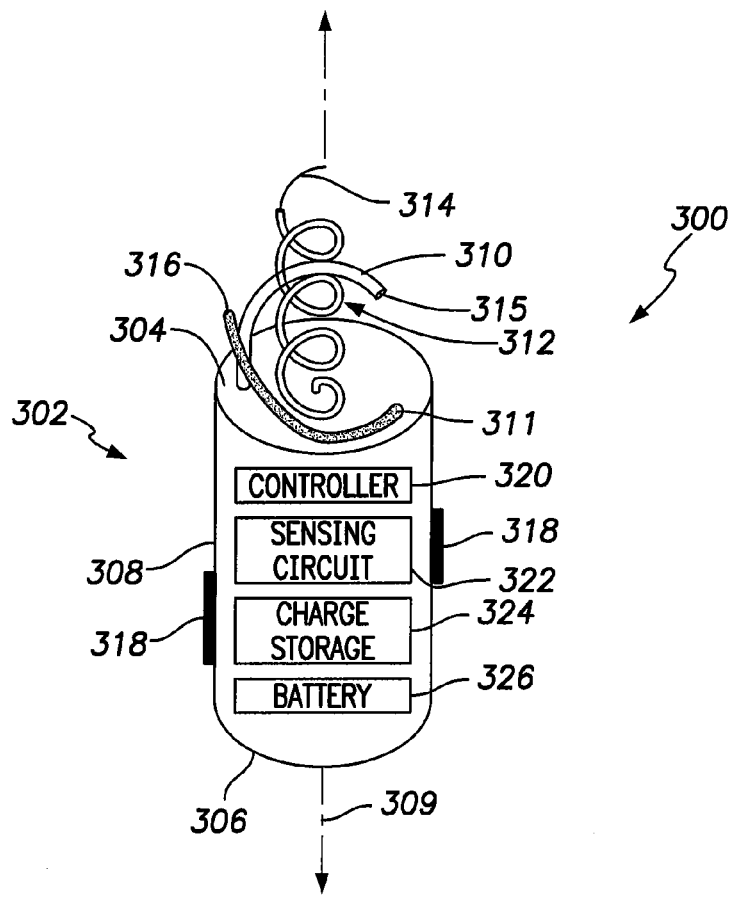
FIGS. 7A and 7B illustrate an LIMD in more detail with an alternative electrode configuration formed in accordance with an embodiment.
Figure 7B:
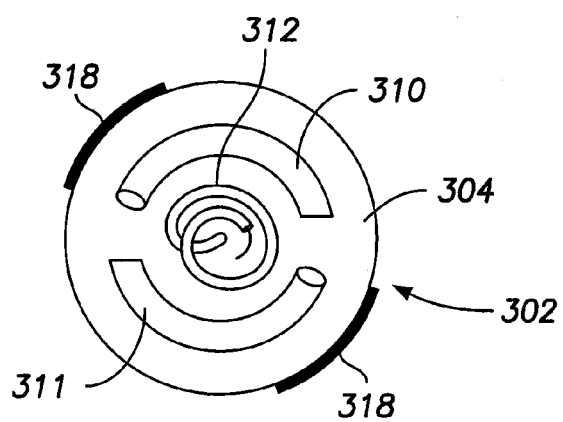

FIGS. 7A and 7B illustrate an LIMD 300 in more detail with an alternative electrode configuration formed in accordance with an embodiment. FIG. 7A illustrates a side perspective view oriented with a base 304 facing upward. FIG. 7B illustrates a bottom plan view of the LIMD 300. The LIMD 300 comprises a housing 302 having a base 304, a top end 306, and an intermediate shell 308 extending between the base 304 and the top end 306. The shell 308 is elongated and tubular in shape and extends along a longitudinal axis 309.

The base 304 includes one or more electrodes 310-312 securely affixed thereto and projected outward. For example, the outer electrodes 310, 311 may be formed as large semicircular spikes or large gauge wires that wrap only partially about the inner electrode 312. The electrodes 310, 311 may be located on opposite sides of, and wound in a common direction with, the inner electrode 312. The first or outer electrodes 310, 311 are provided directly on the housing 302 of the LIMD 300 at a first position, namely at or proximate a periphery of the base 304 of the housing. The outer electrodes 310, 311 are positioned near the periphery of the base 304 such that, when the LIMD 300 is implanted in the local chamber (e.g., right atrium), the outer electrodes 310, 311 engage the local chamber wall tissue at tissue of interest for a local activation site that is near the surface of the wall tissue, and that is within the conduction network of the local chamber in which the LIMD 300 is implanted (e.g., RV). The outer electrodes 310, 311 are physically separated or bifurcated from one another and have separate distal outer tips 315, 316. The outer electrodes 310, 311 are electrically joined to one another (i.e., common), but are electrically separated from the inner electrode 312.

The second or inner electrode 312 is also provided directly on the housing 302 of the LIMD 300 at a second position, namely at or proximate to a central portion of the base 304. The inner electrode 312 is positioned near the center of the base 304 and is elongated such that, when the LIMD 300 is implanted in the local chamber, the inner electrode 312 extends a majority of the way through the wall tissue (e.g., septum) until reaching tissue of interest near the adjacent chamber wall (e.g., LV). The inner electrode 312 is inserted to a depth such that a distal tip 314 thereof is located at tissue of interest for an activation site that is physiologically coupled to wall tissue of the adjacent chamber (e.g., LV). By located the distal tip 314 of the inner electrode 312 at an adjacent chamber activation site, the inner electrode 312 initiates contraction at a distal activation site within the conduction network of the adjacent chamber without physically locating the LIMD 300 in the adjacent chamber. The inner and outer electrodes 310-312 may be formed as multiple cathode electrodes that are actively fixated to the myocardium.

Optionally, a single anode electrode or multiple anode electrodes 318 may be provided. The anode electrode(s) 318 may be located along one or more sides of the shell 308, and/or on the top end 306 of the LIMD 300.

The LIMD 300 includes a charge storage unit 324 and sensing circuit 322 within the housing 302. The sensing circuit 322 senses intrinsic activity, while the charge storage unit 324 stores high or low energy amounts to be delivered in one or more stimulus pulses. The electrodes 310-312 may be used to deliver lower energy or high energy stimulus, such as pacing pulses, cardioverter pulse trains, defibrillation shocks and the like. The electrodes 310-312 may also be used to sense electrical activity, such as physiologic and pathologic behavior and events and provide sensed signals to the sensing circuit 322. The electrodes 310-312 are configured to be joined to an energy source, such as a charge storage unit 324. The electrodes 310-312 receive stimulus pulse(s) from the charge storage unit 324. The electrodes 310-312 may be the same or different size.

The LIMD 300 includes a controller 320, within the housing 302, to cause the charge storage unit 324 to deliver activation pulses through one or each of the electrodes 310-312, based on information from the sensing circuit 322, such that activation pulses delivered from the inner electrode 312 are timed to initiate activation in the adjacent chamber. The stimulus pulses may be delivered synchronously to local and distal activation sites in the local and distal conduction networks such that stimulus pulses delivered at the distal activation site are timed to cause contraction of the adjacent chamber in a predetermined relation to contraction of the local chamber.

The controller 320 may operate the LIMD 300 in various modes, such as in select pacemaker modes, select cardiac resynchronization therapy modes, a cardioversion mode, a defibrillation mode and the like. For example, a typical pacing mode may include DDIR, R, DDOR and the like, where the first letter indicates the chamber(s) paced (e.g., A: Atrial pacing; V: Ventricular pacing; and D: Dual-chamber (atrial and ventricular) pacing). The second letter indicates the chamber in which electrical activity is sensed (e.g., A, V, or D). The code O is used when pacemaker discharge is not dependent on sensing electrical activity. The third letter refers to the response to a sensed electric signal (e.g., T: Triggering of pacing function; I: Inhibition of pacing function; D: Dual response (i.e., any spontaneous atrial and ventricular activity will inhibit atrial and ventricular pacing and lone atrial activity will trigger a paced ventricular response) and O: No response to an underlying electric signal (usually related to the absence of associated sensing function)). The fourth letter indicates rate responsive if R is present.

The housing 302 also include a battery 326 that supplies power to the electronics and energy to the change storage unit 324.

Figure 8:
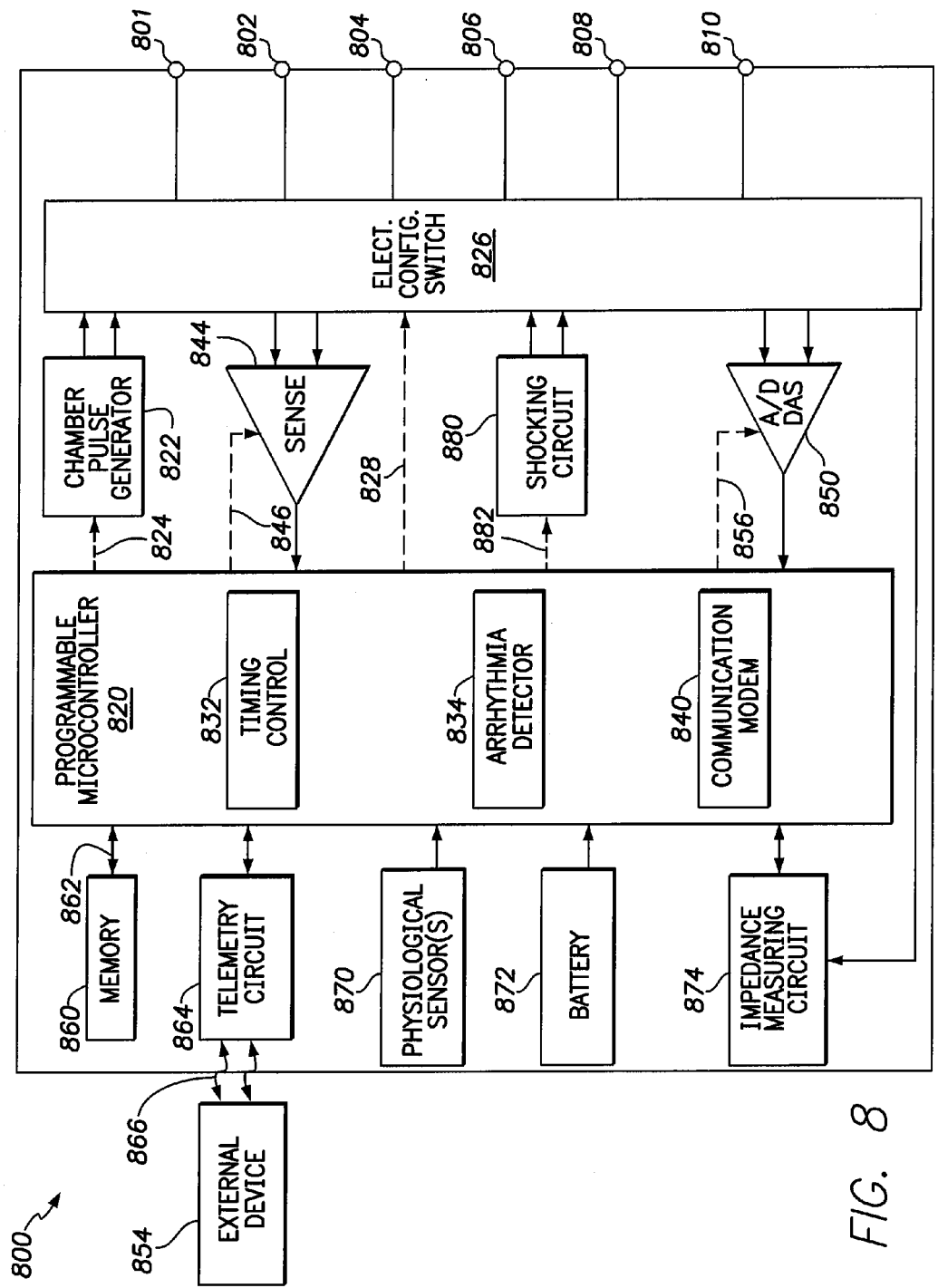
FIG. 8 illustrates an exemplary LIMD configured for dual-chamber functionality from a primary location within a single chamber of the heart.

FIG. 8 shows an exemplary LIMD 800 configured for dual-chamber functionality from a primary location within a single chamber of the heart. For example, the LIMD 800 may be implemented as a pacemaker, equipped with both atrial and ventricular sensing and pacing circuitry. Alternatively, the LIMD 800 may be implemented with a reduced set of functions and components. For instance, the LIMD 800 may be implemented without ventricular sensing and pacing. The LIMD 800 may also be implemented with an increased set of functions. For example, if the LIMD 800 includes a coil type electrode, the LIMD may be configured to include cardioversion and/or shocking therapy capability.

The LIMD 800 has a housing 801 to hold the electronic/computing components. The housing 801 (which is often referred to as the "can", "case", "encasing", or "case electrode") may be programmably selected to act as the return electrode for certain stimulus modes. Housing 801 further includes a plurality of terminals 802, 804, 806, 808, 810 that interface with electrodes of the LIMD. The LIMD 800 includes a programmable microcontroller 820 that controls various operations of the LIMD 800, including cardiac monitoring and stimulation therapy. Microcontroller 820 includes a microprocessor (or equivalent control circuitry), RAM and/or ROM memory, logic and timing circuitry, state machine circuitry, and I/O circuitry.

LIMD 800 further includes a first chamber pulse generator 822 that generates stimulation pulses for delivery by one or more electrodes coupled thereto. The pulse generator 822 is controlled by the microcontroller 820 via control signal 824. The pulse generator 822 is coupled to the select electrode(s) via an electrode configuration switch 826, which includes multiple switches for connecting the desired electrodes to the appropriate I/O circuits, thereby facilitating electrode programmability. The switch 826 is controlled by a control signal 828 from the microcontroller 820.

In the example of FIG. 8, a single pulse generator 822 is illustrated. Optionally, the LIMD 800 may include multiple pulse generators, similar to pulse generator 822, where each pulse generator is coupled to one or more electrodes and controlled by the microcontroller 820 to deliver select stimulus pulse(s) to the corresponding one or more electrodes.

Microcontroller 820 is illustrated as including timing control circuitry 832 to control the timing of the stimulation pulses (e.g., pacing rate, atrio-ventricular (AV) delay etc.). The timing control circuitry 832 may also be used for the timing of refractory periods, blanking intervals, noise detection windows, evoked response windows, alert intervals, marker channel timing, and so on. Microcontroller 820 also has an arrhythmia detector 834 for detecting arrhythmia conditions. Although not shown, the microcontroller 820 may further include other dedicated circuitry and/or firmware/software components that assist in monitoring various conditions of the patient's heart and managing pacing therapies.

The LIMD 800 includes sensing circuitry 844 selectively coupled to one or more electrodes through the switch 826. The sensing circuitry detects the presence of cardiac activity in the right chambers of the heart. The sensing circuitry 844 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit 802 to sense low amplitude signal characteristics of atrial fibrillation. Switch 826 determines the sensing polarity of the cardiac signal by selectively closing the appropriate switches. In this way, the clinician may program the sensing polarity independent of the stimulation polarity.

The output of the sensing circuitry 844 is connected to the microcontroller 820 which, in turn, triggers or inhibits the pulse generator 822 in response to the absence or presence of cardiac activity. The sensing circuitry 844 receives a control signal 846 from the microcontroller 820 for purposes of controlling the gain, threshold, polarization charge removal circuitry (not shown), and the timing of any blocking circuitry (not shown) coupled to the inputs of the sensing circuitry.

The LIMD 800 further includes an analog-to-digital (A/D) data acquisition system (DAS) 850 coupled to one or more electrodes via the switch 826 to sample cardiac signals across any pair of desired electrodes. The data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). The data acquisition system 850 is controlled by a control signal 856 from the microcontroller 820.

The microcontroller 820 is coupled to a memory 860 by a suitable data/address bus 862. The programmable operating parameters used by the microcontroller 820 are stored in memory 860 and used to customize the operation of the LIMD 800 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 808 within each respective tier of therapy.

The operating parameters of the LIMD 800 may be non-invasively programmed into the memory 860 through a telemetry circuit 864 in telemetric communication via communication link 866 with the external device 854. The telemetry circuit 864 allows intracardiac electrograms and status information relating to the operation of the LIMD 800 (as contained in the microcontroller 820 or memory 860) to be sent to the external device 854 through the established communication link 866.

The LIMD 800 can further include magnet detection circuitry (not shown), coupled to the microcontroller 820, to detect when a magnet is placed over the unit. A magnet may be used by a clinician to perform various test functions of the LIMD 800 and/or to signal the microcontroller 820 that the external device 854 is in place to receive or transmit data to the microcontroller 820 through the telemetry circuits 864.

The LIMD 800 may be equipped with a communication modem (modulator/demodulator) 840 to enable wireless communication with a remote device, such as a second implanted LIMD in a master/slave arrangement, such as described in U.S. Pat. No. 7,630,767. In one implementation, the communication modem 840 uses high frequency modulation. As one example, the modem 840 transmits signals between a pair of LIMD electrodes, such as between the can 800 and anyone of the electrodes connected to terminals 802-810. The signals are transmitted in a high frequency range of approximately 20-80 kHz, as such signals travel through the body tissue in fluids without stimulating the heart or being felt by the patient. The communication modem 840 may be implemented in hardware as part of the microcontroller 820, or as software/firmware instructions programmed into and executed by the microcontroller 820. Alternatively, the modem 840 may reside separately from the microcontroller as a standalone component.

The LIMD 800 can further include one or more physiologic sensors 870. Such sensors are commonly referred to as "rate-responsive" sensors because they are typically used to adjust pacing stimulation rates according to the exercise state of the patient. However, the physiological sensor 870 may further be used to detect changes in cardiac output, changes in the physiological condition of the heart, or diurnal changes in activity (e.g., detecting sleep and wake states).

A battery 872 provides operating power to all of the components in the LIMD 800. The battery 872 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 872 also desirably has a predictable discharge characteristic so that elective replacement time can be detected. As one example, the unit 802 employs lithium/silver vanadium oxide batteries.

The LIMD 800 further includes an impedance measuring circuit 874, which can be used for many things, including: impedance surveillance during the acute and chronic phases for proper LIMD positioning or dislodgement; detecting operable electrodes and automatically switching to an operable pair if dislodgement occurs; measuring respiration or minute ventilation; measuring thoracic impedance; detecting when the device has been implanted; measuring stroke volume; and detecting the opening of heart valves; and so forth. The impedance measuring circuit 874 is coupled to the switch 826 so that any desired electrode may be used.

The microcontroller 820 further controls a shocking circuit 880 by way of a control signal 882. The shocking circuit 880 generates shocking pulses of low (e.g., up to 0.5 joules), moderate (e.g., 0.5-10 joules), or high energy (e.g., 811 to 40 joules), as controlled by the microcontroller 820. Such shocking pulses are applied to the patient's heart 808 through shocking electrodes, if available on the LIMD. It is noted that the shock therapy circuitry is optional and may not be implemented in the LIMD, as the various LIMDs described above and further below will typically not be configured to deliver high voltage shock pulses. On the other hand, it should be recognized that an LIMD may be used within a system that includes backup shock capabilities, and hence such shock therapy circuitry may be included in the LIMD.

Figure 9A:
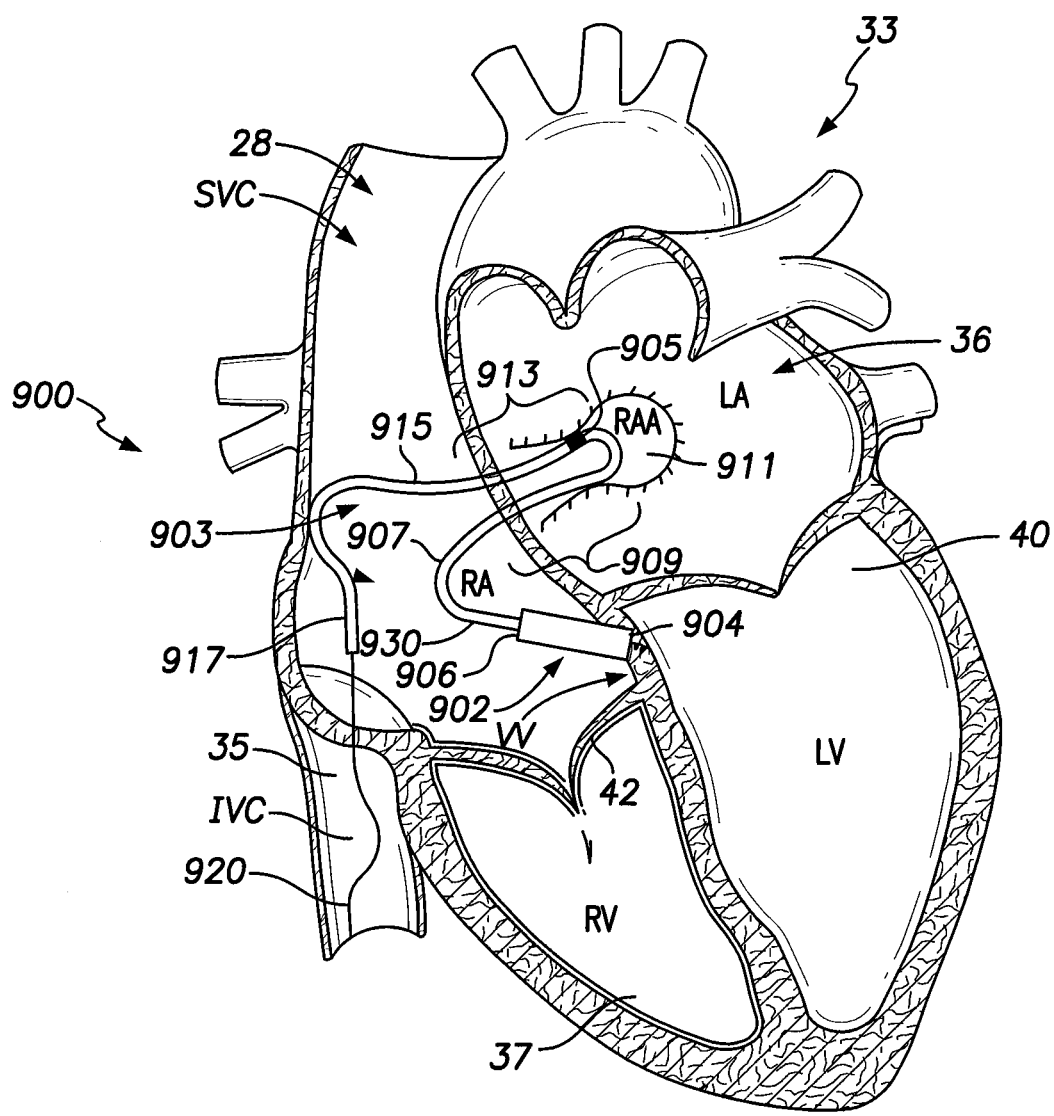
FIG. 9A illustrates a sectional view of a patient's heart having implanted therein an LIMD formed in accordance with an alternative embodiment.

FIG. 9A illustrates a sectional view of a patient's heart having implanted therein an LIMD 900 formed in accordance with an alternative embodiment. The LIMD 900 comprises a housing 902 configured to be implanted entirely within a single local chamber of the heart (e.g., the RA, LA, etc.). The housing 902 includes a base end 904 and a top end 906. The base end 904 includes an active fixation member, such as a helix, that is illustrated to be implanted in the ventricular vestibule (VV). A shaped intra-cardiac (IC) device extension 903 extends from the top end 906 of the housing 902. The IC device extension 903 comprises an elongated body that may be tubular in shape and may include a metal braid provided along at least a portion of the length therein (as explained herein in more detail). The extension body including a transition sub-segment, an active interim-segment and a stabilizer end-segment, all of which are illustrated in a deployed configuration and some of which are preloaded against anatomical portions of tissue of interest.

The IC device extension 903 is formed with shape memory characteristics that allow the IC device extension 903 to transform between a collapsed state, in which the IC device extension assumes a substantially linear shape, and an expanded state, in which the IC device extension assumes a multiple curved shape.

The IC device extension includes a short stem 930 that extends a short distance from the top end 906 of the housing 902. The stem 930 merges into a first curved segment 907. The first curved segment 907 merges into and is followed by a first generally linear region 909 that extends laterally from the housing 902, along a lateral axis, until merging with a second curved segment 911. The second curved segment 911 merges into and is followed by a second generally linear region 913 that extends along a second lateral direction.

One or more electrodes 905 are located along the second curved segment 911. Optionally, the electrode(s) may be provided in the region proximate to the junction of the second curved segment 911 and the second linear region 913. Optionally, one or more electrodes 905 may be provided along the second linear region 913.

The second linear region 913 merges with and extends to a third curved segment 915. The third curved segment 915 follows an extending "slow" arc and then terminates at a tail end 917 of the IC device extension 903. The shaped IC device extension 903 is formed into a pre-loaded shape in which the first, second and third curved segments 907, 911 and 915 extend along desired arcuate paths and project from longitudinal/lateral axes at desired pitch, roll and yaw angles, where the pitch, roll and yaw angles are measured from reference angular positions.

With continued reference to FIG. 9A, the LIMD 900 is configured to place the housing 902 in the lower region of the right atrium between the OS and IVC with a distal helix electrode, on the housing 902, in the ventricular vestibule to provide ventricular pacing and sensing. The IC device extension 903 is configured (length wise and shape wise) such that the second curved segment 911 may be implanted within the right atrial appendage (RAA), along with those portions of the first and second linear regions 909, 913 near the second curved segment 911. The configuration in FIG. 9A places the electrode 905 in the RAA to allow for right atrial pacing and sensing. The configuration in FIG. 9A also places the proximal portion of the third curved segment 915 against a wall of the SVC or IVC to provide overall stability to the LIMD 900.

An IRM 920 is securely attached to the tail end 917 of the IC device extension 903. The IRM 920 is configured in the same manner as explained herein.

During an extraction process, the retrieval tool 140 is inserted in the same manner as discussed above, and advanced over the IRM 920. The retrieval tool 140 is advanced over the tail end 917 of the IC device extension 903. The proximal end of the IRM 920 may be held by the physician as the retrieval tool 140 is slid over the IC device extension 903 in order to prevent the IC device extension 903 from moving within the RA away from the distal end of the IRM 920. As the retrieval tool 140 advances over the IC device extension 903, the IC device extension 903 returns to a straight substantially linear alignment within the lumen in the retrieval tool 140 (similar to the shape exhibited by the IC device extension 903 during implant). The retrieval tool 140 advances over the curved segment 915, straight segment 913, curved segment 911, straight segment 909, curved segment 907, stem 930 until reaching the top end 906 of the LIMD 900.

Optionally, the retrieval tool 140 may then be securely attached to the LIMD 900 and manipulated (as discussed above) to rotate or otherwise cause the LIMD 900 to detach from the cardiac tissue. As a further option, the retrieval tool 140 may not be securely attached to the LIMD 900. Instead, the retrieval tool 140 may be held adjacent the top end 906 of the housing 902. Optionally, the retrieval tool 140 may be slid partially or wholly over the housing 902.

The LIMD 900 may then be rotated indirectly by causing the IC device extension 903 to rotate. For example, a separate tool such as an extension gripper may be inserted into the femoral vein either within, or adjacent to, the lumen of the retrieval tool 140. The separate extension gripper may be securely attached to the tail end 917 of the IC device extension 903 and manipulated (e.g., rotated) to cause the IC device extension 903 and thus the housing 902 to rotate or otherwise be manipulated until becoming detached from the cardiac tissue.

Figure 9B:
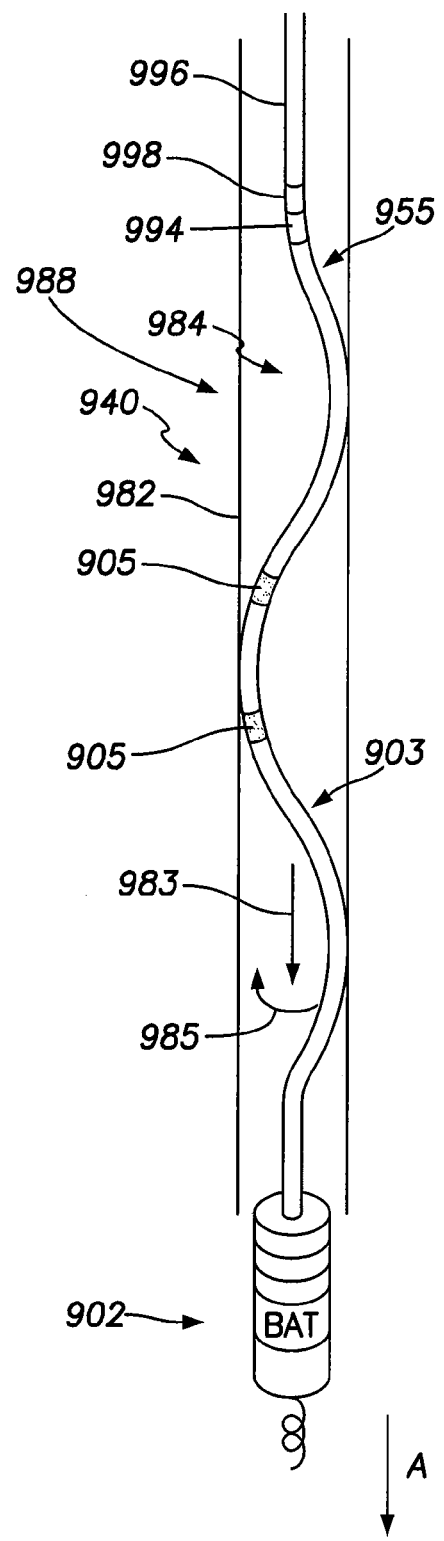
FIG. 9B illustrates a retrieval tool formed in accordance with an alternative embodiment.

FIG. 9B illustrates a retrieval tool 940 formed in accordance with an alternative embodiment. The retrieval tool 940 includes a sheath or catheter 988 having a lumen 984 provided therein. The sheath 988 is advanced until the IC device extension 903 is held within the sheath 988, with the housing 902 still exposed wholly or partially beyond the sheath 988. A pusher rod 996 is slidably inserted into the retrieval tool 940 and maneuvered to directly engage the tail end of the IC device extension 903. Optionally, the pusher rod 996 may be extended beyond and alongside the IC device extension 903 until the pusher rod 996 directly engages the top end of the LIMD 900. For example, the pusher rod 996 may linearly translate the IC device extension 903 and LIMD 900 along a longitudinal axis 983 and rotate the IC device extension 903 and LIMD 900 about the rotational axis 985. The pusher rod 996 includes a pusher tip connector 998 that is configured to securely engage the distal 955 of the IC device extension body 903. The distal end 955 includes a connection member 994 that is configured to securely mate with the pusher tip connector 998 (e.g., through a threaded connection, an interference fit, or the like). The pusher rod 996 may extend into and retract from the sheath 982 under a physician's control. The pusher rod 996 and LIMD 900 are located at opposite ends of the extension body. However, rotational force applied by the pusher rod 996 on the distal end 955 of the extension body is substantially all transferred to the LIMD 900. This rotational force may be used to rotate and detach the LIMD 900 to the wall tissue by unscrewing the active fixation member, such as a helical anchor, a coil, a helical wire having a sharp point, a hook, a barb, or the like.

Figure 10A:
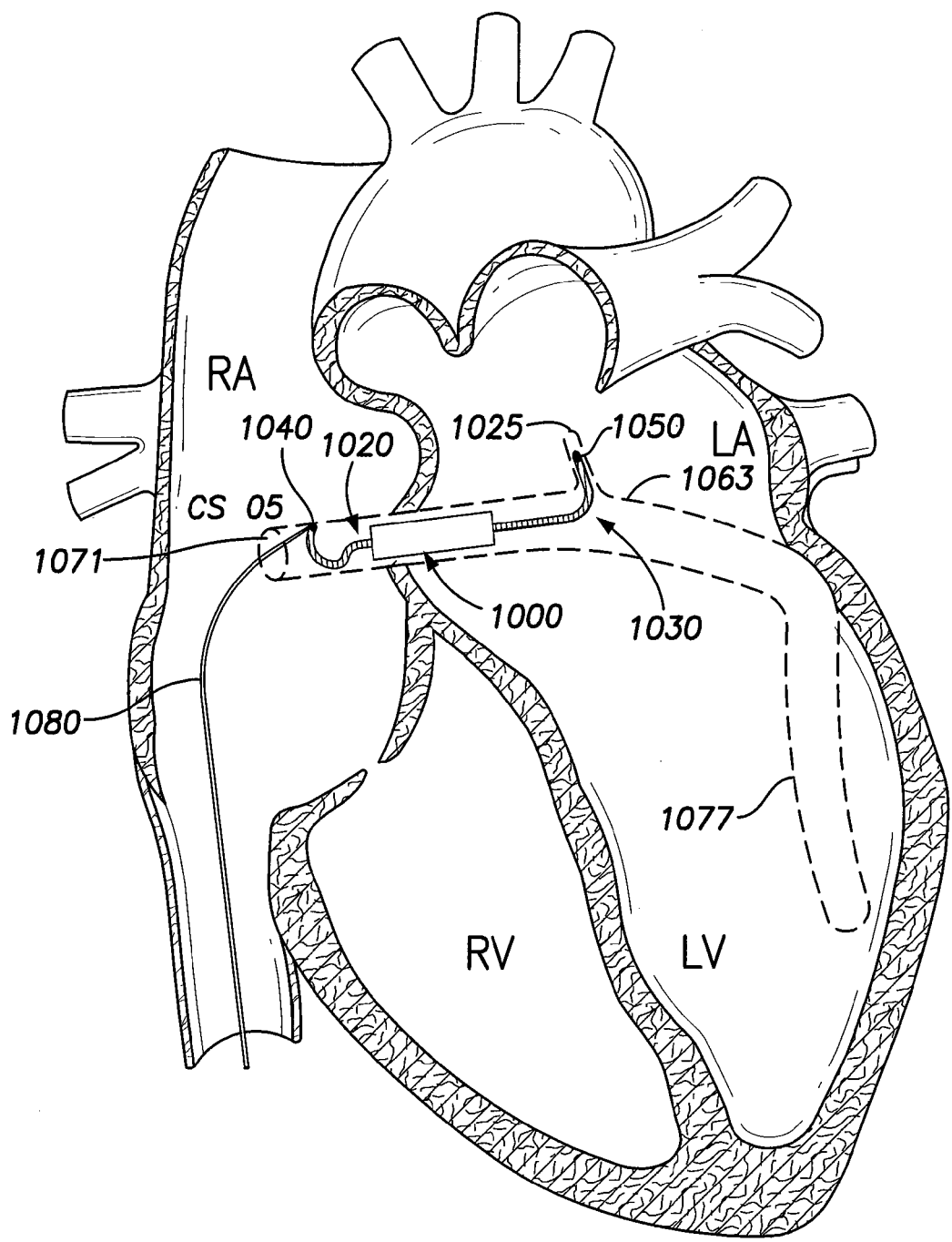
FIG. 10A illustrates a side view of the heart formed in accordance with an alternative embodiment.

FIG. 10A illustrates a side view of the heart with an LIMD 1000 formed in accordance with an alternative embodiment. The LIMD 1000 may have been placed through the superior vena cava (SVC) or inferior vena cava (IVC) through the right atrium of the heart, into ostium 1071 (representing the juncture of the coronary sinus and the RA), into the coronary sinus (CS) 1063. The coronary sinus branches into various tributary vessels such as the lateral veins, great cardiac vein, middle cardiac vein, small cardiac vein, anterior inter-ventricular veins and the like. In FIG. 10A, the lateral cardiac vein 1077 and vein of Marshall 1025 are denoted with reference numbers as examples. The lateral cardiac vein 1077 extends along the LV toward the LV apex. The vein of Marshall 1025 extends along a side of the LA.

The LIMD 1000 includes intracardiac device extensions (ICDE) 1020 and 1030 electrically and mechanically coupled to opposed ends of the LIMD 1000 and extending in opposite directions therefrom. The ICDEs 1020 and 1030 have one or more electrodes provided thereon. In the example of FIG. 10A, tip electrodes 1040 and 1050 are shown provided on the distal ends of the ICDEs 1020 and 1030, respectively. The ICDE 1030 has an outer portion that is deflected and extends into a vessel branching from the coronary sinus, namely the vein of Marshall 1025, thereby locating the electrode 1050 proximate to the LA.

In accordance with embodiments herein, the LIMD 1000 and ICDEs 1020 and 1030 are small enough to be delivered into the coronary sinus through the OS without interfering with normal blood flow in the CS. One or more electrodes may be attached to opposite ends of the ICDEs 1020 and 1030 and electrically connected to the control system within the LIMD 1000 via flexible extension bodies made of biocompatible and biostable materials, such as polymers and the like. The extension bodies of the ICDEs 1020 and 1030 separate electrodes at suitable distances based upon desired activation sites and chambers of interest. As one example, one ICDE 1030 may locate an electrode 1050 proximate to the left atrium to form an LA electrode. The LA electrode is provided on an extension body that is preshaped to bend up or transversely (relative to the longitudinal axis of the LIMD) in order to be able to be securely positioned or wedged into the vein of Marshall or another vessel of interest. An opposed ICDE 1020 has one or more electrodes 1040 thereon that are configured to be located proximate to or within the RA, thereby forming an RA electrode. The RA electrode is provided on an extension body that may be preshaped into an S-shape or other similar shape. The RA and LA electrodes are configured to be able to sense and pace the RA and LA in a simultaneous or coordinated manner from within the coronary sinus (and vein of Marshall) as shown in FIG. 10A.

In one embodiment, the housing of the LIMD 1000 may be formed as a flexible leadless pacer body for which the dimensions of the leadless pacer are designed to fit in the CS anatomy. As one example, the LIMD 1000 may be formed with a long and thin tubular housing with multiple sections, each of which includes various portions of the LIMD functionality, such as the electronics, battery, storage capacitors and the like. Flexible connectors may be utilized to interconnect the separate segments of the long thin tubular body. Optionally, the overall housing of the LIMD 10 may be formed as one body. In various embodiments, the LIMD 10 may be formed with a rigid metallic body in ring structure that contains a battery, capacitors and electronics. Flexible biocompatible polymer body extensions are connected to opposite ends of the LIMD 1000 housing and have the RA and LA electrodes provided on distal ends thereof.

An IRM 1080 is attached to the proximal end of the ICDE 1020. The IRM 1080 extends through the ostrium 1071, the RA and along the IVC. The IRM 1080 is configured in accordance with embodiments described herein. The distal end of the ICDE 1020 may include a mating feature configured to securely attach to a retrieval tool and/or pusher rod. Optionally, the LIMD 1000 may include a mating feature configured to securely attach to a retrieval tool and/or pusher rod.

The controller of the LIMD 1000 may be configured to provide bi-atrial pacing and sensing. The LIMD 1000 may perform bi-polar pacing of the RA and LA with pacing and/or sensing vectors formed between the RA electrode to the LIMD housing, between the LA electrode and the LIMD housing, and/or between the RA and LA electrodes. The system may be configured to perform dual chambered pacing and sensing (e.g., in a DDD mode). As explained hereafter, embodiments herein provide an LIMD 10 that may utilize passive fixation mechanisms to maintain the device in place. For example, the flexible ICDE may be designed to bend toward the LA and to be placed into the vein of Marshall to afford passive fixation. The LIMD 1000 may be configured to sense in the LA and RA, identify AF and in response thereto deliver atrial antitachycardia pacing (ATTP) therapy. For example, by pacing the LA through the vein of Marshall, the system may afford suppression of AF given that the LA electrode is located close to the AF origin.

Figure 10B:
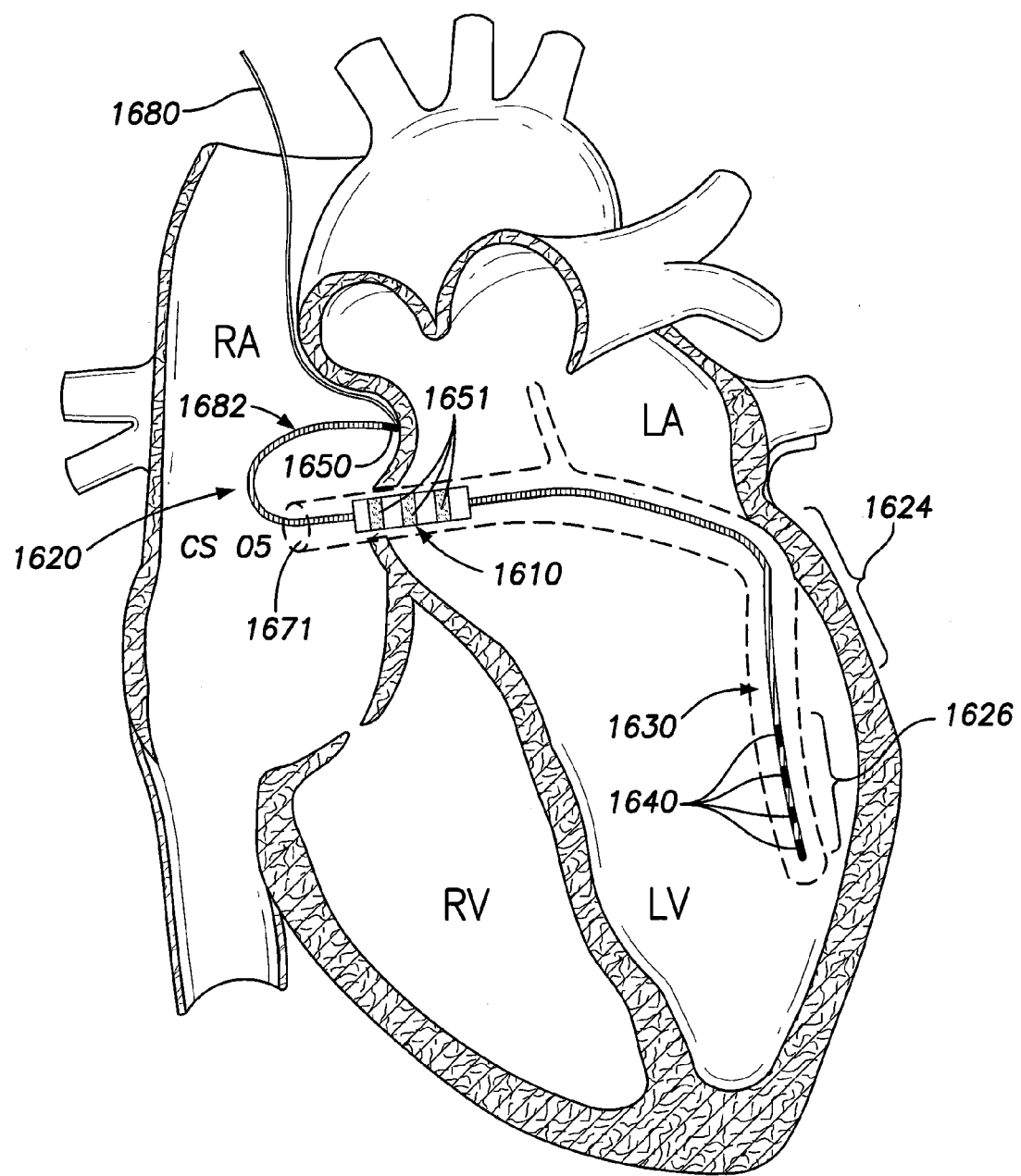
FIG. 10B illustrates a system form in accordance with an alternative embodiment.

FIG. 10B illustrates a system form in accordance with an alternative embodiment. In FIG. 10B, the LIMD 1610 is located in the coronary sinus, but proximate to the OS. The LIMD 1610 has first and second ICDEs 1620 and 1630 extending from opposite ends thereof. The ICDE 1630 is formed longer than those discussed above in connection with other embodiments to be implanted into the lateral or great cardiac vein near the LV. The ICDE 1620 has been modified to be longer to extend through the OS back into the RA, such as to the RAA. As shown in FIG. 10B, the ICDE 1620 has a longer extension body that is preformed into a C or U shape with the distal end 1682 wrapping back and abutting against the wall of the RA such that an electrode 1650 securely abuts against the wall of the RA at an activation site of interest. As one example, the electrode 1650 may extend into the right atrial appendage and abut against an electrically engaged tissue in the RAA. Alternatively, the ICDE 1620 may be shaped such that the extension body wraps back until the distal end 1682 is located proximate to the atrial septum such that the electrode 1650 electrically engages the atrial septum.

The ICDE 1630 includes an active segment 1626 that is joined by a transition segment 1624 to the LIMD 1610. The active segment 1626 includes multiple electrodes 1640, such as in a quadripole configuration. The electrodes 1640 may be electrically coupled to the sensing and pacing circuits in the LIMD 1610 through individual or a common conductors extending along the transition segment 1624. The electrodes 1640 pace and sense in the LV. The housing of the LIMD 1610 includes one or more electrodes 1651 positioned to afford LA pacing and sensing.

An IRM 1680 is attached to the proximal end of the ICDE 1620. The IRM 1680 extends through the ostrium 1671, the RA and along the IVC. The IRM 1680 is configured in accordance with embodiments described herein. The distal end of the ICDE 1620 may include a mating feature configured to securely attach to a retrieval tool and/or pusher rod. Optionally, the LIMD 1610 may include a mating feature configured to securely attach to a retrieval tool and/or pusher rod.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A leadless implantable medical device (LIMD) system comprising;
- a housing having a distal end and a proximal end, the distal end configured to be actively secured to tissue in an implant chamber of a heart;
- at least one electrode configured to perform at least one of sensing and pacing of at least one chamber of the heart;
- a processor to control sensing and pacing operations;
- an indwelling retrieval mechanism (IRM) having a distal end coupled to the proximal end of the housing, the IRM having a body configured to extend from the heart, along a vessel and exit the vessel at an exit/re-entry point;
- the IRM having a proximal end configured to be anchored at a temporary anchor site to at least one of subcutaneous tissue and muscle while the LIMD is implanted;
- the body of the IRM being formed of a flexible biocompatible and biostable material and having sufficient strength to maintain a desired level of structural integrity for a duration of time that the LIMD is implanted;
- a catheter having first and second lumen, the first lumen to receive the IRM; and
- an LIMD gripper device loaded into the second lumen and advanced until projecting from an open end of the catheter, a distal end of the LIMD gripper device coupling to a proximal end of the LIMD.

2. The LIMD system of claim 1 wherein the IRM body comprises a conducive core electrically coupled to the processor the core being configured to transmit electrical communications from the LIMD.

3. The LIMD system of claim 1, wherein the IRM is formed of a flexible biocompatible and biostable material.

4. The LIMD system of claim 1, wherein the IRM is formed of a monofilament or multistrand suture thread.

5. The LIMD system of claim 1, further comprising, on the IRM, a non-thrombogenic coating having a strength to survive a duration of a time in which the LIMD is implanted.

6. A leadless implantable medical device (LIMD) system comprising;
- a housing having a distal end and a proximal end, the distal end configured to be actively secured to tissue in an implant chamber of a heart;
- at least one electrode configured to perform at least one of sensing and pacing of at least one chamber of the heart;
- a processor to control sensing and pacing operations;
- intra-cardiac (IC) device extension having a distal end coupled to a proximal end of the LIMD, the device extension including one or more electrodes coupled to the processor to perform at least one of sensing and pacing of at least one chamber of the heart;
- an indwelling retrieval mechanism (IRM) having a distal end coupled to a proximal end of the IC device extension, the IRM having a body configured to extend from the heart, along a vessel and exit the vessel at an exit/re-entry point;
- the IRM having a proximal end configured to be anchored at a temporary anchor site to at least one of subcutaneous tissue and muscle while the LIMD is implanted;
- a catheter having first and second lumen, the first lumen to receive the IRM; and
- an LIMD gripper device loaded into the second lumen and advanced until projecting from an open end of the catheter, a distal end of the LIMD gripper device coupling to the proximal end of the LIMD.

* * * * *